(12) United States Patent
Neoh et al.

(10) Patent No.: US 12,070,559 B2
(45) Date of Patent: *Aug. 27, 2024

(54) DRAINAGE CATHETER HUB WITH A SEMI-COMPRESSED SUTURE SEAL

(71) Applicant: Cook Medical Technologies LLC, Bloomington, IN (US)

(72) Inventors: Wen Hong Neoh, Bloomington, IN (US); Gregory A. Frankland, Bloomington, IN (US); Scott K. Philhower, Cincinnati, OH (US); Arman H. Valaie, Bloomington, IN (US)

(73) Assignee: Cook Medical Technologies LLC

( * ) Notice: Subject to any disclaimer, the term of this patent is extended or adjusted under 35 U.S.C. 154(b) by 0 days.

This patent is subject to a terminal disclaimer.

(21) Appl. No.: 18/062,131

(22) Filed: Dec. 6, 2022

(65) Prior Publication Data

US 2023/0173228 A1 Jun. 8, 2023

Related U.S. Application Data

(63) Continuation of application No. 16/529,157, filed on Aug. 1, 2019, now Pat. No. 11,517,712, which is a
(Continued)

(51) Int. Cl.
*A61M 25/00* (2006.01)
*A61M 25/01* (2006.01)
(Continued)

(52) U.S. Cl.
CPC .... *A61M 25/0097* (2013.01); *A61M 25/0043* (2013.01); *A61M 25/0133* (2013.01);
(Continued)

(58) Field of Classification Search
CPC .......... A61M 25/0097; A61M 25/0043; A61M 25/0147; A61M 25/0163
See application file for complete search history.

(56) References Cited

U.S. PATENT DOCUMENTS

9,079,006 B1 * 7/2015 Ovcharchyn ..... A61M 25/0097
10,369,330 B2 * 8/2019 Neoh ................ A61M 25/0097
(Continued)

*Primary Examiner* — Tasnim Mehjabin Ahmed
(74) *Attorney, Agent, or Firm* — Woodard, Emhardt, Henry, Reeves & Wagner, LLP (57) ABSTRACT

Described are drainage catheter hub devices which seal the hub from leakage when connected to a catheter. The catheter hub includes a hub body having an aperture with a sealing element mounted therein and a fluid passageway that communicates with the aperture. The fluid passageway and sealing element are configured to receive a tension member. A lever arm attached to the hub body is operable to secure the position of the tension member in the sealing element in a locked position or allow movement of the tension member through the sealing element in an unlocked position. The lever arm is configured to engage and compress the sealing element to block fluid flow through the sealing element and the aperture when the lever arm is in any position. The hub body may include a centering tab to align the tension member along a longitudinal axis of the hub body.

18 Claims, 5 Drawing Sheets

Related U.S. Application Data continuation of application No. 15/416,545, filed on Jan. 26, 2017, now Pat. No. 10,369,330.

(60) Provisional application No. 62/293,930, filed on Feb. 11, 2016.

(51) Int. Cl.
*A61M 25/09* (2006.01)
*A61M 27/00* (2006.01)
*A61M 39/10* (2006.01)

(52) U.S. Cl.
CPC ........ *A61M 25/0147* (2013.01); *A61M 25/09* (2013.01); *A61M 27/00* (2013.01); *A61M 39/1011* (2013.01); *A61M 2025/0063* (2013.01); *A61M 2025/09125* (2013.01); *A61M 2039/1072* (2013.01); *A61M 2205/3334* (2013.01)

(56) References Cited

U.S. PATENT DOCUMENTS

| | | | |
|---|---|---|---|
| 11,517,712 B2 * | 12/2022 | Neoh | A61M 27/00 |
| 2006/0212009 A1 * | 9/2006 | Accisano | A61M 27/00 |
| | | | 604/326 |

* cited by examiner

DRAINAGE CATHETER HUB WITH A SEMI-COMPRESSED SUTURE SEAL

CROSS REFERENCE TO RELATED APPLICATIONS

This application is a continuation of U.S. application Ser. No. 16/529,157, filed Aug. 1, 2019, now issued Dec. 6, 2022, U.S. Pat. No. 11,517,712 which is a continuation of U.S. application Ser. No. 15/416,545, filed Jan. 26, 2017 which claims the benefit of U.S. Provisional Application No. 62/293,930 filed Feb. 11, 2016, each of which is hereby incorporated by reference in its entirety.

BACKGROUND

The present disclosure relates generally to medical technology and in particular aspects to drainage catheter hubs attachable to drainage catheters that prevent leakage of fluids therefrom, and related systems.

Drainage catheters are used in a variety of medical procedures, including various catheterization procedures such as drainage of the bladder, kidney or biliary system, abscesses, other sites of fluid collection, and other minimally invasive procedures. Typical drainage catheters have externally-communicating suture lumens in their hubs with a silicone or rubber plug positioned in the hub that is used to seal around the suture. The silicone or rubber plug is used to seal around the suture and pressure is applied onto the plug for sealing around the suture when the drainage catheter is in a locked position. However, the drainage catheters can be prone to leaking fluids and/or gases, especially when the drainage catheters are in the unlocked state. Moreover due to the slick, smooth nature of certain sutures or tension members, it is very difficult to create a seal around them. Leakage of bodily fluids or other liquids and gases out of the drainage catheter can spread biohazards and compromise patient and user safety. A drainage catheter with a suture communicating externally of a main hub lumen typically requires some active user interaction to prevent leakage or the drainage catheter will leak.

There remain needs for devices, systems and methods for preventing leakage from drainage catheter hubs in any position from a locked position to an unlocked position and any position in between the locked and fully unlocked position without active user interaction. The present disclosure is addressed to those needs.

SUMMARY

The present disclosure provides, in certain aspects, device, methods, and systems for preventing leakage from a drainage catheter hub in any unlocked and locked positions and any position between the fully unlocked and locked positions.

Disclosed is a drainage catheter that includes an elongated tubular member wherein the tubular member has a distal end adapted for insertion into a patient, a proximal end, and a passageway extending longitudinally therethrough, the passageway is sized to receive a tension member therein. The drainage catheter includes a drainage catheter hub attached to the proximal end of the tubular member. The drainage catheter hub includes a sealing element configured to receive the tension member. Some forms of a sealing element include a plug, a stopper, a cap or other structural member that is configured to receive the tension member. Some forms of the tension member include suture, filament material, wire, thread, or other material configured to pass through the sealing element. The catheter hub also includes a lever arm connected to a hub body wherein the hub body defines an aperture sized to receive the sealing element. The aperture extends from and communicates with the passageway of the tubular member to an exterior surface of the hub body wherein the aperture and the passageway are aligned for fluid flow therethrough. The lever arm is configured to move between a locked position wherein the tension member is restrained from movement through the sealing element and an unlocked position wherein the tension member is movable through the sealing element. The lever arm is further configured to compress the sealing element to thereby block fluid flow through the sealing element and the aperture when the lever arm is in either the unlocked or the locked positions or any position between the unlocked and locked positions. Optionally, the lever arm is rotatably connected to the hub body. Also optionally, an angle of rotation for the lever arm relative to a longitudinal axis of the hub body is restricted from 0 degrees in the locked position to about 30 degrees in the unlocked position. Optionally, the hub body includes a post and the lever arm includes a hole sized to receive the post therein to connect the lever arm to the hub body. Electively, the exterior surface of the hub body includes a centering tab configured to align the tension member along a longitudinal axis of the hub body. In this embodiment, the centering tab includes a vertical leg that extends from the exterior surface of the hub body to connect to a horizontal leg with a groove therebetween sized to retain the tension member. Optionally, the exterior surface of the hub body includes a plurality of hub serrated teeth positioned between the aperture and the centering tab, and an interior surface of the lever arm includes a plurality of lever arm serrated teeth that are arranged and configured to engage the plurality of hub serrated teeth to retain the tension member aligned along the longitudinal axis of the hub. Also optionally, the aperture includes a base end having a first diameter and in communication with the passageway and a tip end having a second diameter that is larger than the first diameter, the tip end in communication with the exterior surface of the hub, and the aperture having a body portion that spans between the base end and the tip end wherein the body portion has a variable diameter sized to receive a portion of the sealing element therein and to block fluid flow through the base end of the aperture. Electively, the lever arm is configured to compress the sealing element to block fluid flow through the sealing element and the aperture when the lever arm is in any position.

Also disclosed is a drainage catheter hub for use with a tension member and a drainage catheter, wherein the drainage hub includes a hub body that defines a fluid passageway in communication with an aperture, the hub body is adapted for attachment to the drainage catheter wherein the fluid passageway and the drainage catheter are aligned for fluid flow therethrough. The catheter hub also includes a sealing element configured to receive the tension member wherein the sealing element is sized for and positioned in an aperture of the hub body. The catheter hub includes a lever arm that is connected to the hub body. The lever arm is configured to move relative to the hub body such that the tension member is restrained from movement through the sealing element when the lever arm is in a first position and the tension member is movable through the sealing element when the lever arm is in a second position. The lever arm is further configured to engage and compress the sealing element to form a first seal around the tension member and a second seal with the aperture to block fluid flow through the sealing element and the aperture of the hub body when the lever arm is in any position.

Also disclosed is a drainage catheter hub for use with a tension member and a drainage catheter that includes a hub body defining a fluid passageway in communication with an aperture wherein the hub body is adapted for attachment to the drainage catheter. The fluid passageway and the drainage catheter are aligned for fluid flow therethrough. The catheter hub includes a sealing element configured to receive the tension member wherein the sealing element is sized for and positioned in the aperture of the hub. The catheter hub includes a lever arm attached to the hub body. The lever arm is moveable between an unlocked position wherein the tension member is movable through the sealing element and a locked position wherein the tension member is restrained from movement through the sealing element. The lever arm is further configured to press against the sealing element to compress the sealing element to block fluid flow through the sealing element and the aperture of the hub body. Optionally, an exterior surface of the hub body includes a plurality of hub serrated teeth, and an interior surface of the lever arm includes a plurality of lever arm serrated teeth that are arranged and configured to engage the plurality of hub serrated teeth to retain the tension member aligned along a longitudinal axis of the hub. Also optionally, an exterior surface of the hub body includes a centering tab configured to align the tension member along a longitudinal axis of the hub body and an interior surface of the lever arm includes a pocket sized to receive the centering tab in the locked position. Electively, the lever arm is rotatably connected to the hub body and an angle of rotation for the lever arm relative to a longitudinal axis of the hub body is restricted from 0 degrees in the locked position to about 30 degrees in the unlocked position. Optionally, the lever arm includes a pair of protrusions to engage the hub body and retain the lever arm in a locked position.

Other objects, embodiments, forms, features, advantages, aspects, and benefits of the present disclosure shall become apparent from the detailed description and drawings included herein.

DESCRIPTION OF THE SELECTED EMBODIMENTS

While the present disclosure may be embodied in many different forms, for the purpose of promoting an understanding of the principles of the present disclosure, reference will now be made to the embodiments illustrated in the drawings, and specific language will be used to describe the same. It will nevertheless be understood that no limitation of the scope of the claims is thereby intended. Any alterations and further modifications in the described embodiments and any further applications of the principles of the present disclosure as described herein are contemplated as would normally occur to one skilled in the art to which the disclosure relates.

In the following discussion, the terms "proximal" and "distal" will be used to describe the opposing axial ends of the catheter, as well as the opposing axial ends of component features, such as the drainage catheter hub. The term "proximal" is used in its conventional sense to refer to the end of the catheter, or component feature, that is closest to the operator during use. The term "distal" is used in its conventional sense to refer to the end of the catheter, or component feature, that is initially inserted into the patient, or that is closest to the patient during use.

In certain aspects, the present disclosure provides devices, methods and systems for providing access to a drainage catheter, preventing leakage through a catheter hub, and securing sutures external to the patient's body in a variety of medical procedures. Many medical procedures utilizing drainage catheters do so in combination with catheter hubs that may leak bodily fluids in an unlocked position and possibly spread biohazards and compromise patient and user safety.

The present application prevents liquid and air leakage through the suture exit site on drainage catheter hubs when the suture or tension member has not been secured or when the drainage catheter hub has not been locked. Due to the slick, smooth nature of certain monofilament sutures or tension members, it is very difficult to effectively seal around them to prevent leakage of liquid or air. This application discloses a catheter hub with a moveable lever arm that has a locked position and an unlocked position, whereby the range-of-motion of the lever arm, when unlocked, is restricted so that it maintains pressure on the sealing element or suture plug, thereby compressing the sealing element or suture plug around the suture and compressing the sealing element within an aperture of the catheter hub, creating a seal around the suture and a seal between the sealing element and the aperture, even in the unlocked position. One advantage of this application is that the catheter hub is constantly and continuously sealed such that liquid or air does not leak out where the suture or the sealing element exit the catheter hub, regardless of any position the lever arm is in. In other words, if the lever arm is in the locked position or the unlocked position the aperture in the sealing element is compressed such that air or liquid does not leak through it.

In certain aspects, the present disclosure provides for a drainage catheter including a catheter or a tubular member, a suture or tension member, and a drainage catheter hub. The drainage catheter hub includes a hub body that defines an aperture sized to receive a sealing element wherein the aperture extends from an exterior surface of the hub body to communicate with a fluid passageway of the hub body. The catheter hub includes a lever arm that is configured to move between a locked position wherein the tension member is restrained from movement through the sealing element and an unlocked position wherein the tension member is movable through the sealing element. The lever arm is also configured to compress the sealing element to block fluid flow through the sealing element and the aperture when the lever arm is in any position, including the locked and unlocked positions. The sealing element is sized and shaped to fill or crowd an aperture in the hub body. The lever arm, which constantly provides some level of compression on the sealing element creates a seal around the suture or tension member, regardless if the catheter hub is in the locked or unlocked position. In other words, the catheter hub maintains the sealing element in a semi-compressed state when the drainage catheter hub is unlocked. This is important as leakage of bodily fluids or other liquids/gases out of the aperture of the drainage catheter can spread biohazards and compromise patient and user safety. Optionally, the lever arm is rotatably connected to the hub body and an angle of rotation for the lever arm relative to a longitudinal axis of the hub body is restricted from 0 degrees in the first position to about 30 degrees in the second position. Also optionally, the hub body includes a post and the lever arm includes a hole sized to receive the post therein to connect the lever arm to the hub body. Optionally, the sealing element is made of silicone, thermoplastic, or polyisoprene material. Electively, an exterior surface of the hub body includes a centering tab configured to align the tension member along a longitudinal axis of the hub body. Further, the exterior surface of the hub body defines an aperture sized to receive the tension member wherein the aperture is aligned with the centering tab.

Other suture sealing methods that disclose a suture that communicates externally of the main hub lumen typically require some active user interaction to prevent leakage or they have small leaks. However, the present application describes a catheter hub that does not require active user interaction. The limited range-of-motion of the lever arm, designed into the hub, applies some pressure on the sealing element without any action from the user, to provide a seal around the suture while the lever arm is still in the unlocked position. The level of compression is enough so that a seal is provided but it is not too much where the suture is hard to pull to tighten an end of the tubular member. The suture is passed through the lumen of the catheter or tubular member, through the sealing element, through a first aperture on the lever arm, between the lever arm and the hub body, and in some embodiments through an aperture on the lever arm, to exit away from the catheter to enable one to pull a free end of the suture. The lever arm is rotatably connected to the hub body to secure the suture therebetween, such that the suture is substantially prevented from moving when the lever arm is in the locked position. However, when the lever arm is in the unlocked position, the suture is freely movable through the sealing element. In any position between and including the locked and unlocked positions, the lever arm is configured to maintain pressure on the sealing element to seal the aperture and the lumen in the sealing element through which the suture passes. As such, the amount of pressure that the lever arm applies to the sealing element will decrease from the greatest amount in a fully locked position to the least amount in a fully unlocked position.

Figure 7:
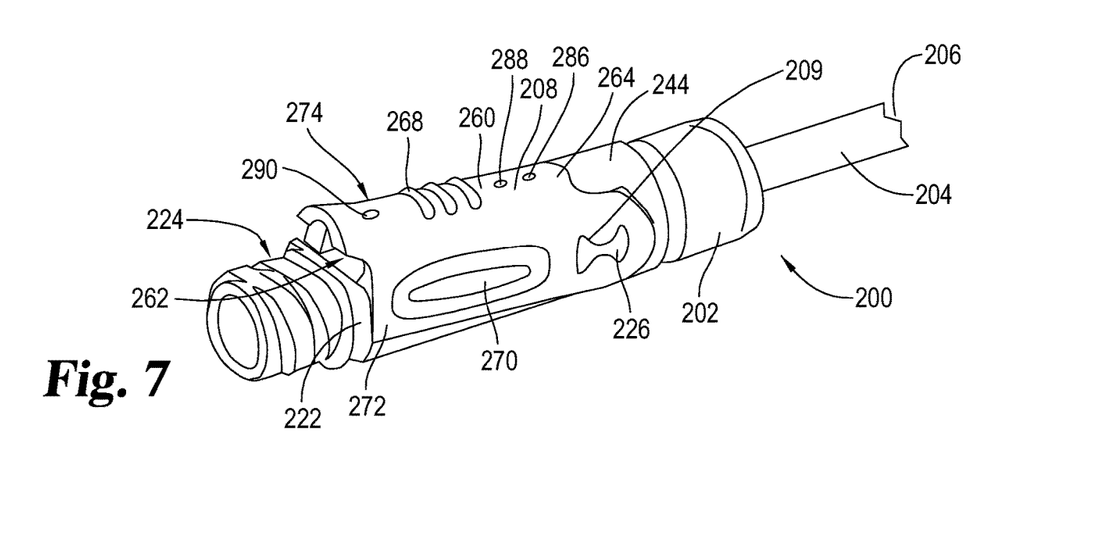
FIG. 7 is a perspective view of a second embodiment of a drainage catheter hub in a locked configuration with a tubular member attached to the drainage catheter hub.
Figure 8:
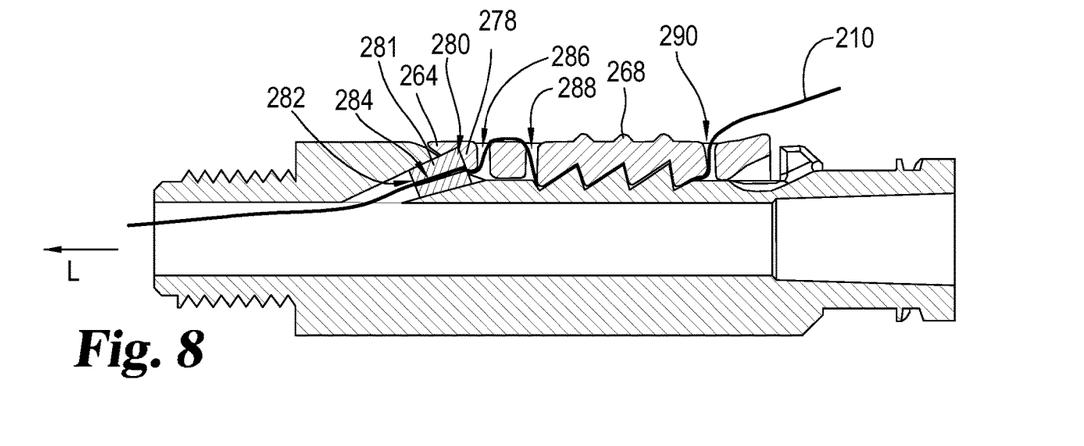
FIG. 8 is a cross-sectional view of the catheter hub of FIG. 7 in a locked configuration with a tension member.
Figure 9:
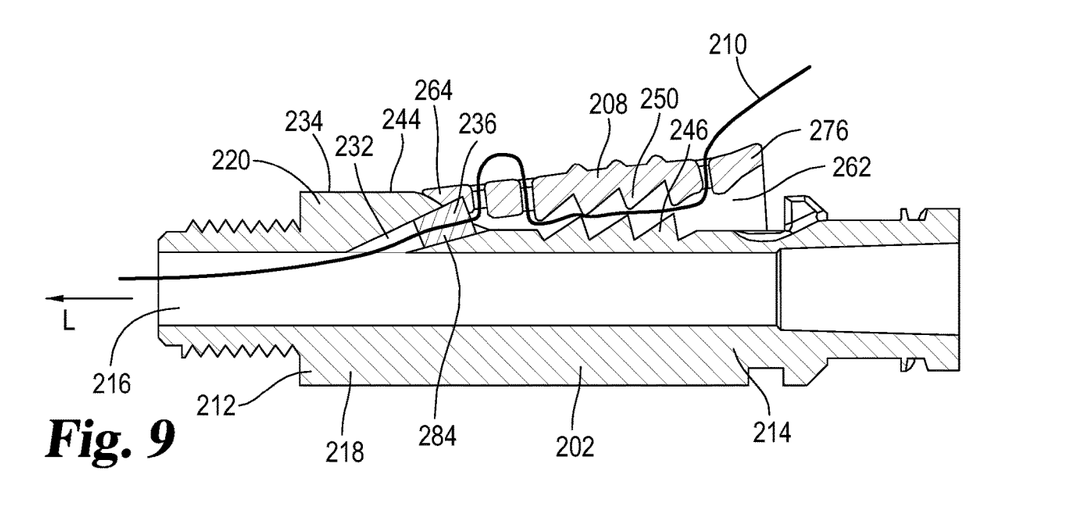
FIG. 9 is a cross-sectional view of the catheter hub of FIG. 7 in an unlocked configuration with a tension member.
Figure 10:
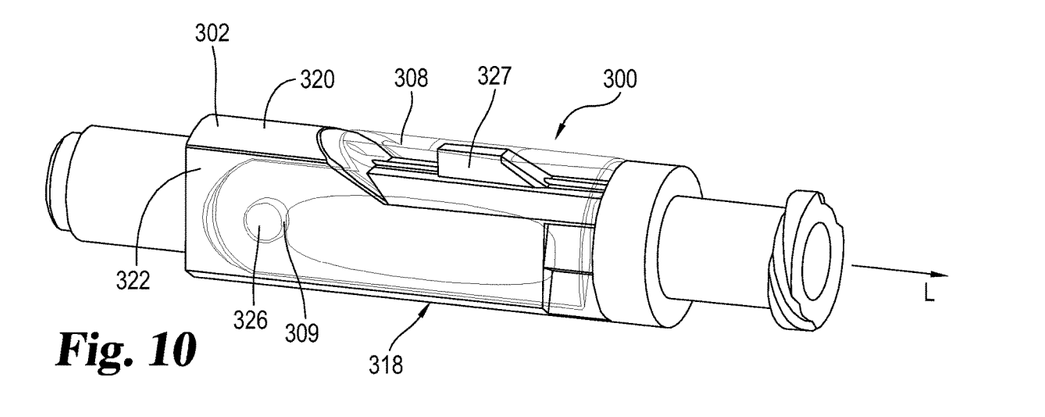
FIG. 10 is a perspective view of a third embodiment of a drainage catheter hub in a locked configuration.
Figure 11:
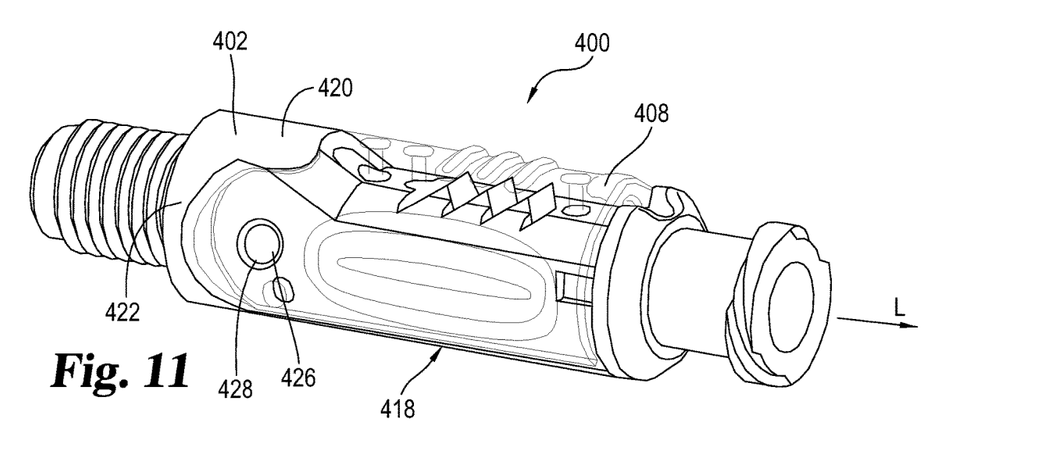
FIG. 11 is a perspective view of a fourth embodiment of a drainage catheter hub in a locked configuration.

FIGS. 1 through 6 illustrate one non-limiting example of a catheter hub according to one embodiment of the present disclosure. FIGS. 7 through 9 show a second non-limiting example of a catheter hub according to a second embodiment of the present disclosure. FIG. 10 illustrates a third non-limiting example of a catheter hub according to another embodiment of the present disclosure. FIG. 11 illustrates a fourth non-limiting example of a catheter hub according to another embodiment of the present disclosure.

With reference now to FIGS. 1 through 6, there is shown a drainage catheter hub assembly 100 according to one embodiment of the present disclosure. In this illustrative arrangement, the catheter hub assembly 100 includes a hub body 102 that is configured to engage with a proximal end 104 of a tubular member 106 to form a catheter system. The hub body 102 also includes a luer lock end 115 that is configured for attachment to a drainage collection system. The catheter hub assembly 100 includes a lever arm 108 that is configured to attach to the hub body 102 to clamp a suture or a tension member 110 therebetween. The catheter hub assembly 100 also includes a sealing element 136 wherein the lever arm 108 is configured to press against the sealing element 136.

The particular illustrated hub body 102 extends along a longitudinal axis L in a substantially cylindrical fashion between a distal end 112 opposite a proximal end 114. The hub body 102 also defines a fluid passageway 116 that extends between the distal end 112 and the proximal end 114. The fluid passageway 116 is configured to receive a portion of the tension member 110, and enable fluid, and/or gases to pass therethrough. As illustrated, the fluid passageway 116 is substantially cylindrical in cross-sectional shape; however, other shapes or configurations for the cross section are within the scope of this application.

Figure 1:
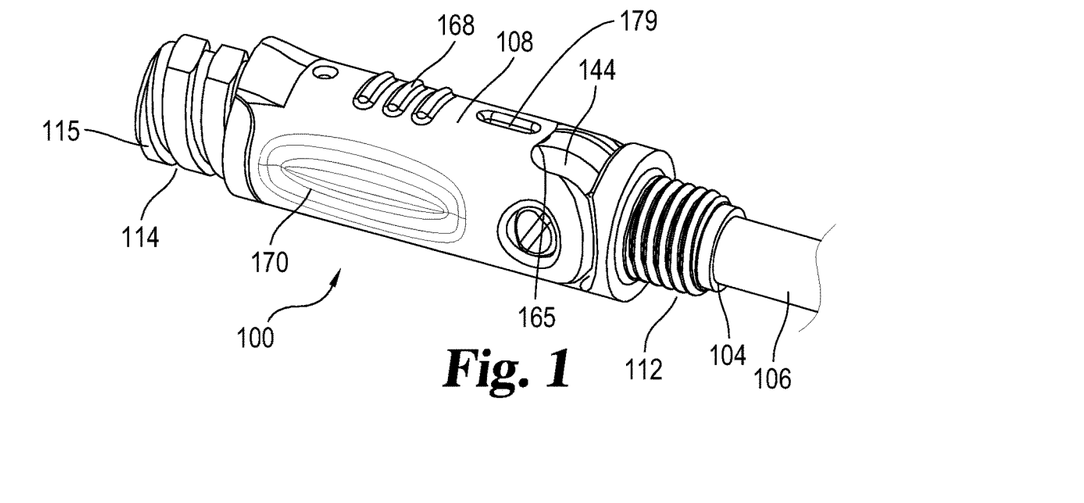
FIG. 1 is a perspective view of a first embodiment of a drainage catheter hub in a locked configuration with a tubular member attached to the drainage catheter hub.
Figure 2:
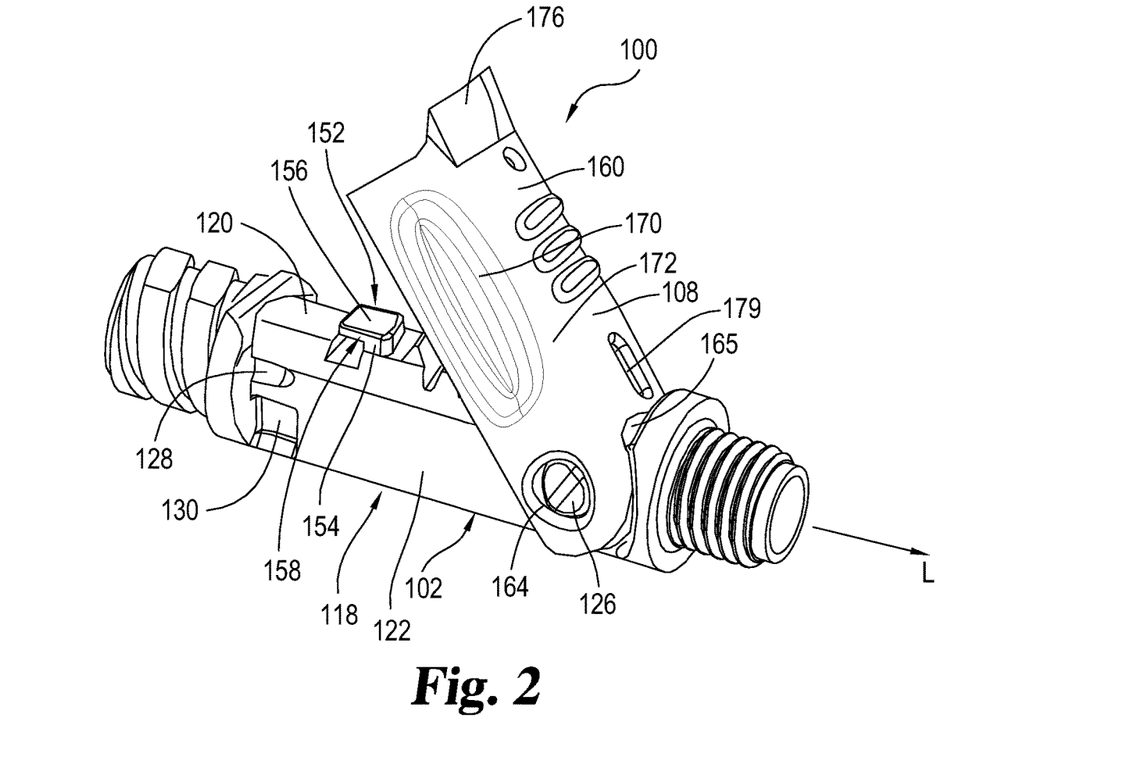
FIG. 2 is a perspective view of the catheter hub of FIG. 1 in an unlocked configuration without a tubular member attached to the drainage catheter hub.
Figure 3:
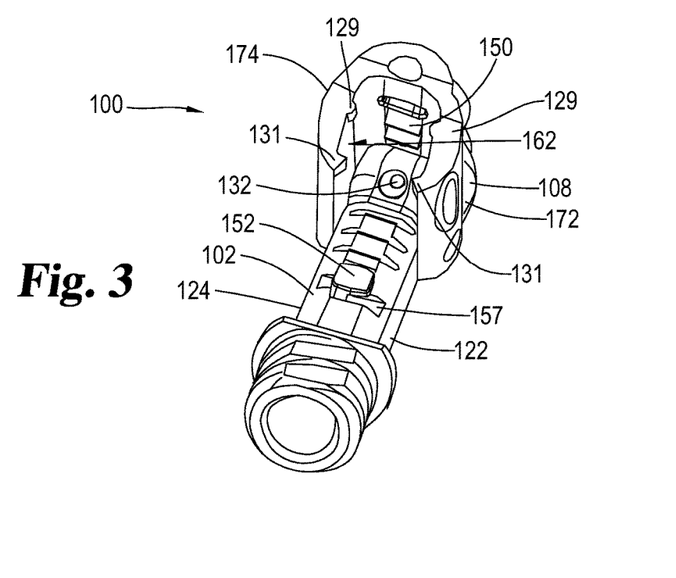
FIG. 3 is a top view of the catheter hub of FIG. 2 rotated counterclockwise.

The hub body 102 also includes a lower body portion 118 opposite an upper portion 120 and a right face 122 opposite a left face 124 wherein the lower and upper portions 118 and 120 and the right and left faces 122 and 124 span between the distal and the proximal ends 112 and 114, respectively. Generally, the lower body portion 118 has a substantially smooth outer surface. Each of the right and left faces 122 and 124, respectively, include a post 126 positioned closer to the proximal end 112. In one form, the post 126 has a cylindrical shape and extends a distance away from the right and left faces 122 and 124. The post 126 is sized and configured to engage and retain the lever arm 108 such that the lever arm 108 is able to rotate about the post 126 as desired by the user or medical practitioner. In this embodiment, the diameter of the post 126 can range in size between 0.05 inches to about 0.25 inches. In one form, the diameter of the post 126 is 0.125 inches. Each of the right and left faces 122 and 124, respectively, also include a first recess 128 spaced a distance from a second recess 130 wherein the first recess 128 and the second recess 130 are positioned closer to the proximal end 114. The first recess 128 is sized and configured to retain an interior first nub 129 on the lever arm 108 and the second recess 130 is sized and configured to retain an interior second nub 131 on the lever arm 108 to thereby retain the lever arm 108 in a closed or locked position against the upper portion 120.

Figure 4:
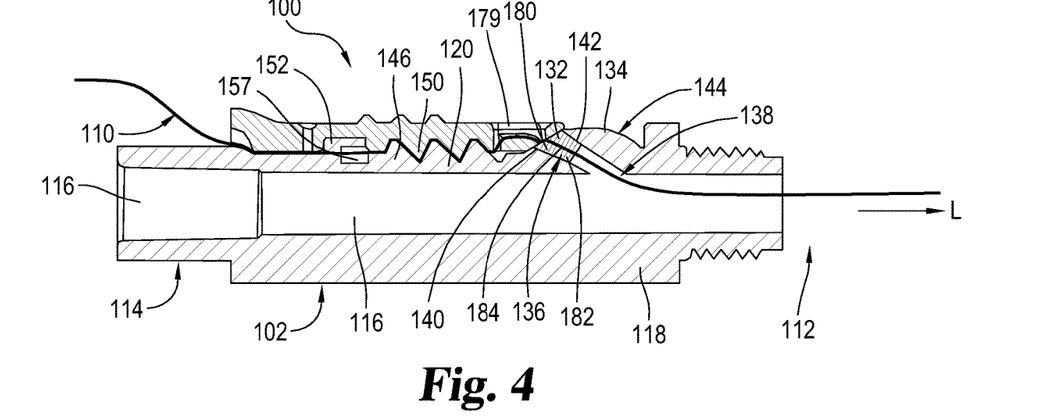
FIG. 4 is a cross-sectional view of the catheter hub of FIG. 1 with a tension member.
Figures 5, 6:
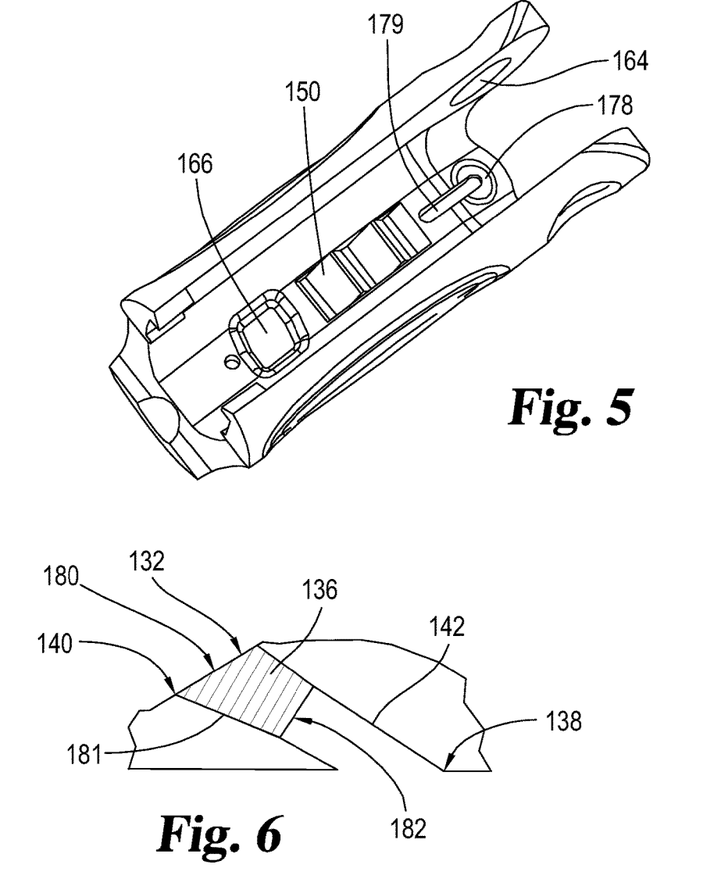
FIG. 5 is a bottom view of a lever arm from the catheter hub of FIG. 1.
FIG. 6 is a partial cross sectional view of the aperture and sealing element of the catheter hub of FIG. 1.

The upper portion 120 defines an aperture 132 having tapered walls 142 that span from the fluid passageway 116 to an exterior surface 134 of the hub body 102. The aperture 132 is sized to receive and retain a sealing element 136. The aperture 132 includes a cylindrical interior shaft portion 138 that engages the fluid passageway 116. The aperture 132 is tapered cylindrically and spans from a narrower diameter at the fluid passageway 116 to a larger diameter at the exterior surface 134. As such, the aperture 132 includes an exterior shaft portion 140 that engages the exterior surface 134. In this embodiment, the exterior shaft portion 140 has the largest diameter and the interior shaft portion 138 which has the smallest diameter. The exterior shaft portion 140 has a diameter of about 0.075 inches but can be larger or smaller as desired. As explained in more detail below, the sealing element 136 has a shape that corresponds to the shape of exterior shaft portion 140, the tapered walls 142, and the interior shaft portion 138 of aperture 132 to enable a greater area for compression by the lever arm 108 as compared to a tubular sealing element and aperture.

The upper portion 120 also includes a protrusion 144 that projects outwardly. Generally the protrusion 144 has a substantially rounded shape; however, other embodiments may have a square, rectangular, oval, or other shape. As described below, the protrusion 144 receives a proximal end of the lever arm 108 to thereby limit movement of the lever arm 108. The exterior shaft portion 140 of the aperture 132 is located near the protrusion 144.

The upper portion 120 includes a plurality of hub serrated teeth 146 positioned adjacent the aperture 132 and the protrusion 144. The plurality of hub serrated teeth 146 are sized and arranged to engage a corresponding number of a plurality of lever arm serrated teeth 150 on the lever arm 108 as described below. In the illustrated configuration, each of the plurality of hub serrated teeth 146 has a substantially triangular shape. However, other configurations can include rectangular, circular, curved, or polygonal shape for each of the plurality of hub serrated teeth 146. Additionally, the plurality of hub serrated teeth 146 and plurality of lever arm serrated teeth 150 are configured to retain the tension member 110 between them and stop movement of the tension member 110 when the lever arm 108 is in the locked or closed position.

The upper portion 120 includes a centering tab 152 positioned between the plurality of hub serrated teeth 146 and the proximal end 114. The centering tab 152 includes a vertical leg 154 that extends away from the exterior surface 134. The centering tab 152 also includes a horizontal leg 156 that is mounted on the end of the vertical leg 154. In one embodiment, the centering tab 152 includes a joint or groove 158 that is located under the horizontal leg 156 at the end of the vertical leg 154 to receive the tension member 110. Generally, the vertical leg 154 and the horizontal leg 156 are rectangular in shape but may have an alternative configuration or combination of shapes including cylindrical, triangular, or polygonal. In any configuration, the vertical leg 154 is located on the upper portion 120 adjacent to a centerline of the plurality of hub serrated teeth 146. Additionally, the horizontal leg 156 is oriented to cover or extend over the centerline of the plurality of hub serrated teeth 146 to maintain the position of the tension member 110 in an orientation that is along the centerline of the plurality of hub serrated teeth 146. The upper portion 120 also defines a passage 157 positioned under the centering tab 152. The passage 157 provides a space for the tension member 110 to pass under the centering tab 152 or between the horizontal leg 156 and the exterior surface 134. In one form, the passage 157 is about 0.020 inches by 0.015 inches; other embodiments can include larger or smaller sized passages 157.

Turning now to the lever arm 108, lever arm 108 includes an exterior surface 160 opposite an interior surface 162 and has a length that spans from at least the post 126 to about the first recess 128 and the second recess 130 of the hub body 102 when the lever arm 108 is assembled with the hub body 102. The lever arm 108 forms a U-shape wherein the interior surface 162 is configured to enclose and substantially cover the upper portion 120, the right face 122, and the left face 124. The lever arm 108 includes a hole 164 that is sized and positioned to receive the post 126 therein to attach the lever arm 108 to the hub body 102. Alternatively, the hub body 102 defines a hole and the lever arm 108 includes a post to connect the lever arm 108 to the hub body 102. Other embodiments may include alternative interactive features between the lever arm 108 and the hub body 102 to connect the lever arm 108 to the hub body 102. The lever arm 108 has a recessed portion 165 that is configured to slide over or rotate about the protrusion 144 when the lever arm 108 rotates about the post 126. The recessed portion 165 has a rounded shape to avoid sharp corners for easy assembly of the lever arm 108 to the hub body 102.

To assemble the lever arm 108 onto the hub body 102, the recessed portion 165 enables the lever arm 108 to rotate between 0 degrees to about 50 degrees relative to the longitudinal axis L of the hub body 102. In a working arrangement wherein the catheter hub assembly 100 is fully assembled, the lever arm 108 is rotatable about the post 126 between 0 degrees to "X" degrees, wherein X ranges from a value greater than 0 degrees up to about 30 degrees, relative to the longitudinal axis L of the hub body 102. In one embodiment, X is about 20 degrees. The locked position is defined as 0 degrees wherein suture or tension member 110 is captured and restrained from movement through the sealing element 136 and the lever arm 108 applies the greatest compression on the sealing element 136 to create a seal around the tension member 110 in a lumen 184 and a seal between the sealing element 136 and the aperture 132. The unlocked position is defined as "X" degrees wherein the lever arm 108 allows free passage of the suture or tension member 110 through the sealing element 136; however, the lever arm 108 still applies enough compression on sealing element 136 to provide a seal around the suture or tension member 110. As such, the compression on the sealing element 136 in the unlocked position will be less than in the locked position to allow passage of the tension member 110 while maintaining a seal around the tension member 110 in the lumen 184 in the sealing element 136 and a seal between the sealing element 136 and the aperture 132. The lever arm 108 applies pressure to compress the sealing element 136 and create a seal around the suture or tension member 110 in any position (0 degrees to X degrees) so air or liquid does not leak out where suture or tension member 110 exits the catheter hub assembly 100 and between the sealing element 136 and aperture 132. The lever arm 108 can be locked or unlocked and aperture 132 and the lumen 184 in the sealing element 136 are sealed from air or fluid leakage.

The amount of pressure applied from the lever arm 108 to the sealing element 136 is dependent at least on the position of the sealing element 136 in the aperture 132. If sealing element 136 extends further out of the aperture 132 (or closer to the lever arm 108), then less pressure from the lever arm 108 is needed to seal the sealing element 136 and the aperture 132. If the sealing element 136 is further in or deeper in the aperture 132 (or further away from the lever arm 108), then more pressure from the lever arm 108 is needed to seal the sealing element 136 and the aperture 132.

In the illustrated embodiment, the lever arm 108 includes a plurality of nubs 168 mounted on the exterior surface 160 about midway along the length of the lever arm 108. In the illustrated embodiment, the lever arm 108 also includes a plurality of elongated side nubs 170 mounted on the exterior surface 160 along a right side portion 172 and along a left side portion 174 of the lever arm 108. The plurality of nubs 168 and the plurality of elongated side nubs 170 provide a tactile sensation to a user or medical practitioner when they grip or handle the catheter hub assembly 100. The plurality of nubs 168 and the plurality of elongated side nubs 170 provide a gripping surface for a user such that when a syringe is secured to the catheter hub assembly 100, the user has a gripping surface to hold onto to prevent the catheter hub assembly 100 from rotating. However, other embodiments of the lever arm 108 may not include either the plurality of nubs 168 or the plurality of elongated side nubs 170 or the other embodiments may include one of either the plurality of nubs 168 or the plurality of elongated side nubs 170. The lever arm 108 also includes a rear tab 176 that extends from the exterior surface 160 for engagement by a user's finger or thumb.

The interior surface 162 of the lever arm 108 includes a plurality of lever arm serrated teeth 150 arranged and sized to engage the plurality of hub serrated teeth 146 on the hub body 102 to maintain the position of the tension member 110 in an orientation that is along the centerline of the plurality of hub serrated teeth 146 when the lever arm 108 is in the locked position. As such, the number of the plurality of lever arm serrated teeth 150 correspond to the number of the plurality of hub serrated teeth 146. In the illustrated configuration, each of the plurality of lever arm serrated teeth 150 has a substantially triangular shape. However, other configurations can include rectangular, circular, curved, or polygonal shape for each of the plurality of lever arm serrated teeth 150. Moreover, the shape of each of the plurality of lever arm serrated teeth 150 will complement the corresponding shape of each of the plurality of hub serrated teeth 146. Adjacent to the plurality of lever arm serrated teeth 150, the interior surface 162 also includes a receptacle 166 that is sized to receive the horizontal leg 156 of the centering tab 152 therein. The receptacle 166 has substantially the same shape as the cross section of the horizontal leg 156 and a depth sufficient to receive the horizontal leg 156 and the vertical leg 154.

The interior surface 162 of the lever arm 108 includes an engagement portion 178 adjacent the recessed portion 165. The engagement portion 178 is configured to engage and press against the sealing element 136 when the lever arm 108 is assembled with the hub body 102. The illustrated embodiment of the engagement portion 178 is substantially circular in shape and extends away from the interior surface 162 to form a dome or convex surface. Other embodiments of the engagement portion 178 can have a different shape such as rectangular, oval, or polygonal. In other embodiments, the engagement portion 178 spans across the width of the interior surface 162 to form a band to engage and press against the sealing element 136 when the lever arm 108 is assembled with the hub body 102.

The interior surface 162 of the lever arm 108 includes a pair of interior first nubs 129 wherein a single nub 129 is positioned to engage one of the first recesses 128 on the lever arm 108. The interior surface 162 of the lever arm 108 also includes a pair of interior second nubs 131 wherein a single nub 131 is positioned to engage one of the second recesses 130 on the lever arm 108. The interaction of the interior first nubs 129 with the first recesses 128 and/or the interior second nubs 131 with the second recesses 130 retain the lever arm 108 in a closed or locked position against the upper portion 120 of the hub body 102.

The lever arm 108 also includes a hole 179 that is sized to receive the tension member 110 when assembled with the hub body 102. In use on a medical patient, the hole 179 is sized such that a medical practitioner can pull the tension member 110 through the hole 179 to tension the tension member 110 as desired. The hole 179 is positioned near the engagement portion 178 and spans a short distance along a longitudinal axis of the lever arm 108. In the illustrated embodiment, the hole 179 is similar to an oval shaped slot or slit that spans between the exterior surface 160 and the interior surface 162. In other embodiments, the hole 179 can be shaped differently.

The components of a catheter system may be formed with a variety of biocompatible plastic or polymer materials. For example, the components of hub assembly 100, including the hub body 102 and the lever arm 108, may be made from a silicone-based material. The components of hub assembly 100, including the hub body 102 and the lever arm 108, may be manufactured by injection molding using a variety of plastics, including acrylonitrile butadiene styrene (ABS), polybutylene terephthalate (PBT) plastic, and/or polypropylene plastic. In one embodiment, the lever arm 108 is configured to bend or flex more than the hub body 102. In other embodiments, the lever arm 108 and the hub body 102 may be configured differently. Regarding the suture or tension member 110, while suture material in particular will be useful in certain embodiments, a variety of other elongate materials and objects capable of being anchored can be used as an alternative to, or in addition, to suture material. These include various types of cords, filaments, chains, strings, wires and other similar objects having relatively slender profiles for extending through patient tissue.

Turning now to the sealing element 136, the sealing element 136 is sized and shaped to fit in a portion of or fill the entire aperture 132 of the hub body 102. In this embodiment, the sealing element 136 has a base end 180 opposite a tip end 182 and a body portion 181 that spans between the base end 180 and the tip end 182. The sealing element 136 also includes a lumen 184 that spans between the base end 180 and the tip end 182. The base end 180 is cylindrical in shape and has a base diameter that corresponds to and is about the same size as a diameter of the exterior shaft portion 140. In other embodiments, the base diameter of the base end 180 is the same as or slightly larger than the diameter of the exterior shaft portion 140. As such, the base end 180 substantially plugs or seals the exterior shaft portion 140 when the lever arm 108 is in a locked or unlocked position. The tip end 182 is cylindrical in shape and has a diameter that corresponds to a diameter of the interior shaft portion 138. As such, the tip end 182 substantially plugs or seals the interior shaft portion 138 when the lever arm 108 is in a locked or unlocked position. The body portion 181 is configured and sized to fill or plug the aperture 132. As such, the body portion 181 is a tapered cylindrical shape. In the illustrated embodiment, the lumen 184 is sized to receive the tension member 110. Alternatively, the sealing element 136 does not include a lumen but instead a needle with the attached tension member 110 is passed through the sealing element 136 as described below.

The sealing element 136 is made of silicone, thermoplastic, polyisoprene, and/or natural rubber or any combination of these materials; however, other materials can be used. The lumen 184 in the sealing element 136 can be manufactured and assembled with the tension member 110 in a variety of techniques. For example, one manufacturing technique includes cutting or forming the lumen 184 through the sealing element 136 and thereafter threading the tension member 110 through the pre-cut lumen. Another manufacturing technique includes pushing a needle with a tension member 110 attached thereto through the sealing element 136 to create the lumen 184 in the sealing element 136. In this second technique, the sealing element 136 does not have a pre-cut lumen until the needle pushes through the sealing element 136. The lumen 184 in the sealing element 136 is created when the needle with the tension member 110 is pushed through the sealing element 136 to puncture the sealing element 136 and create a lumen. Beneficially both manufacturing techniques will enable the lever arm 108 and the sealing element 136 to seal the lumen 184 around the tension member 110; however, the inventor has found the first technique may require more compression of the sealing element 136 whereas the second technique may require less compression of the sealing element 136. In some embodiments, the second technique creates a lumen that more closely matches the size of the corresponding tension member 110 passing therethrough and there may be less additional space in the lumen around the tension member to fill by compressing the sealing element.

Turning now to the second embodiment of a drainage catheter hub assembly 200 illustrated in FIGS. 7, 8, and 9, wherein the catheter hub assembly 200 is similar to the catheter hub assembly 100. In this illustrative arrangement, the catheter hub assembly 200 includes a hub body 202 that is configured to engage with a proximal end 204 of a catheter tube 206 and a lever arm 208 that is configured to attach to the hub body 202 to clamp a suture or a tension member 210 therebetween. The catheter hub assembly 200 is configured to engage with the catheter tube 206 to form a catheter system.

The hub body 202 extends along a longitudinal axis L in a substantially cylindrical fashion between a distal end 212 opposite a proximal end 214. The hub body 202 also defines a fluid passageway 216 that extends between the distal end 212 and the proximal end 214. The fluid passageway 216 is configured to receive a portion of the tension member 210 and enable fluid and/or gases to pass therethrough. As illustrated, the fluid passageway 216 is substantially cylindrical in cross-sectional shape; however, other shapes or configurations for the cross section are within the scope of this application.

The hub body 202 also includes a lower body portion 218 opposite an upper body portion 220 and a right face 222 opposite a left face 224 wherein the lower and upper body portions 218 and 220 and the right and left faces 222 and 224 span between the distal and the proximal ends 212 and 214, respectively. Generally, the lower body portion 218 has a substantially smooth outer surface. Each of the right and left faces 222 and 224, respectively, include a pivot post 226 positioned closer to the distal end 212. In one form, the post 226 has a bow-tie shape and extends a distance away from the right and left faces 222 and 224. The post 226 is sized and configured to engage a side opening 209 in the lever arm 208 such that the lever arm 208 is able to rotate about the pivot post 226 as desired by the user or medical practitioner. Other embodiments can include different sizes, shapes, and configurations for the interactive features between the lever arm 208 and the hub body 202. For example, the lever arm 208 can include a pivot post and the hub body 202 can include a receptacle sized to receive the pivot post to engage and retain the pivot post therein and the lever arm 208 on the hub body 202.

The upper portion 220 defines an aperture 232 that spans from the fluid passageway 216 to an exterior surface 234 of the hub body 202. The aperture 232 is sized to receive and retain a sealing element 236. The aperture 232 is tapered cylindrically and spans from a narrower diameter at the fluid passageway 216 to a larger diameter at the exterior surface 234. The aperture 232 tapers in cross sectional size from the exterior surface 234 to the fluid passageway 216. Other embodiments can include a different cross-sectional shape for the aperture 232 and a correspondingly sized and shaped sealing element 236.

The upper portion 220 also includes a protrusion 244 that projects outwardly. Generally the protrusion 244 has a substantially rounded shape; however, other embodiments may have a square, rectangular, oval, or other shape. As described below, the protrusion 244 receives a proximal end of the lever arm 208 to thereby limit movement of the lever arm 208.

The upper portion 220 includes a plurality of hub serrated teeth 246 positioned adjacent the protrusion 244 and the aperture 232. The plurality of hub serrated teeth 246 are sized and arranged to engage a corresponding number of a plurality of lever arm serrated teeth 250 on the lever arm 208 as described below. In the illustrated configuration, each of the plurality of hub serrated teeth 246 has a substantially triangular shape. However, other configurations can include rectangular, circular, curved, or polygonal shape for each of the plurality of hub serrated teeth 246. Additionally, the plurality of hub serrated teeth 246 and plurality of lever arm serrated teeth 250 are configured to retain the tension member 210 between them and stop movement of the tension member 210 through the sealing element 236 when the lever arm 208 is in the locked or closed position.

Turning now to the lever arm 208, lever arm 208 includes an exterior surface 260 opposite an interior surface 262 and has a length that spans from the pivot post 226 to about the distal end 212 when the lever arm 208 is assembled with the hub body 202. The lever arm 208 forms a U-shape wherein the interior surface 262 is configured to enclose and substantially cover the upper portion 220, the right face 222, and the left face 224. The lever arm 208 includes a hole 209 that is sized and positioned to receive the pivot post 226 therein to maintain the lever arm 208 attached to the hub body 202. In the illustrated embodiment, the pivot post 226 and the hole 209 have a bow-tie configuration. Other embodiments may include alternative interactive features between the lever arm 208 and the hub body 202. The lever arm 208 has a recessed portion 264 that is configured to slide over or rotate about the protrusion 244 when the lever arm 208 rotates about the pivot post 226. The recessed portion 264 has a rounded shape to avoid sharp corners for easy assembly of the lever arm 208 to the hub body 202.

To assemble the lever arm 208 onto the hub body 202, the recessed portion 264 enables the lever arm 208 to rotate between 0 degrees to about 50 degrees relative to the longitudinal axis L of the hub body 202. In a working arrangement wherein the catheter hub assembly 200 is fully assembled, the lever arm 208 is rotatable about the pivot post 226 between 0 degrees to "X" degrees, wherein X ranges from a value greater than 0 degrees up to about 30 degrees, relative to the longitudinal axis L of the hub body 202. In one embodiment, X is about 20 degrees. The locked position is defined as 0 degrees wherein suture or tension member 210 is captured and restrained from movement through the sealing element 236 and the lever arm 208 applies the greatest compression on the sealing element 236 to create a seal around the tension member 210 in a lumen 284 and a seal between the sealing element 236 and the aperture 232. The unlocked position is defined as "X" degrees wherein the lever arm 208 allows free passage of the suture or tension member 210 through the sealing element 236; however, the lever arm 208 still applies enough compression on sealing element 236 to provide a seal around the suture or tension member 210 and to seal the aperture 232. As such, the compression on the sealing element 236 in the unlocked position will be less than in the locked position to allow passage of the tension member 210 while maintaining a seal around the tension member 210 in the lumen 284 in the sealing element 236 and a seal between the sealing element 236 and the aperture 232. In any position (0 degrees to X degrees), the lever arm 208 applies pressure to compress the sealing element 236 and create a seal around the suture or tension member 210 so air or liquid does not leak out where suture or tension member 210 exits the catheter hub assembly 200.

The amount of pressure applied from the lever arm 208 to the sealing element 236 is dependent at least on the position of the sealing element 236 in the aperture 232. If sealing element 236 extends further out of the aperture 232 (or closer to the lever arm 208), then less pressure is needed to seal the sealing element 236 and the aperture 232. If the sealing element 236 is further in or deeper into the aperture 232 (or further away from the lever arm 208), then more pressure against the sealing element 236 is needed to seal the sealing element 236 and the aperture 232.

In the illustrated embodiment, the lever arm 208 includes a plurality of nubs 268 mounted on the exterior surface 260 about midway along the length of the lever arm 208. In the illustrated embodiment, the lever arm 208 also includes a plurality of elongated side nubs 270 mounted on the exterior surface 260 along a right side portion 272 and along a left side portion 274 of the lever arm 208. The plurality of nubs 268 and/or the plurality of elongated side nubs 270 provide a tactile sensation to a user or medical practitioner when they grip or handle the catheter hub assembly 200. The plurality of nubs 268 and the plurality of elongated side nubs 270 provide a gripping surface for a user such that when a syringe is secured to the catheter hub assembly 200, the user has a gripping surface to hold onto to prevent the catheter hub assembly 200 from rotating. However, other embodiments of the lever arm 208 may not include either the plurality of nubs 268 or the plurality of elongated side nubs 270 or the other embodiments may include one of either the plurality of nubs 268 or the plurality of elongated side nubs 270. The lever arm 208 also includes a rear tab 276 that extends from the exterior surface 260 for engagement by a user's finger or thumb.

The interior surface 262 of the lever arm 208 includes a plurality of lever arm serrated teeth 250 arranged and sized to engage the plurality of hub serrated teeth 246 to maintain the position of the tension member 210 therebetween. As such, the number of the plurality of lever arm serrated teeth 250 correspond to the number of the plurality of hub serrated teeth 246. In the illustrated configuration, each of the plurality of lever arm serrated teeth 250 has a substantially triangular shape. However, other configurations can include rectangular, circular, curved, or polygonal shape for each of the plurality of lever arm serrated teeth 250. Moreover, the shape of each of the plurality of lever arm serrated teeth 250 will complement the corresponding shape of each of the plurality of hub serrated teeth 246.

The interior surface 262 of the lever arm 208 includes an engagement portion 278 adjacent the recessed portion 264. The engagement portion 278 is configured to engage and press against the sealing element 236 when the lever arm 208 is assembled with the hub body 202. The illustrated embodiment of the engagement portion 278 is recessed into the interior surface 262 to form a receptacle to receive a portion of the sealing element 236. Other embodiments of the engagement portion 278 can have a different shape such as rectangular, oval, or polygonal. In other embodiments, the engagement portion 278 spans across the width of the interior surface 262 to form a band to engage and press against the sealing element 236 when the lever arm 208 is assembled with the hub body 202.

The lever arm 208 also includes a first aperture 286, a second aperture 288, and a third aperture 290 wherein each of the apertures 286, 288, and 290 spans between the interior surface 262 and the exterior surface 260. The first aperture 286 is positioned rearward and adjacent to the recessed portion 264. The second aperture 288 is between the first aperture 286 and the third aperture 290. The third aperture 290 is rearward of the plurality of nubs 268 and forward of the rear tab 276. All of the apertures 286, 288, and 290 are sized to receive the tension member 210 through the lever arm 208.

The components of a catheter system may be formed with a variety of biocompatible polymer materials. For example, the components of hub assembly 200, including the hub body 202 and the lever arm 208, may be made from a silicone-based or plastic material. For example, the hub body 202 and the lever arm 208 can be injection molded using a variety of plastics. In one embodiment, the hub body 202 includes ABS (acrylonitrile butadiene styrene) and/or PBT (polybutylene terephthalate) plastics and the lever arm 208 includes polypropylene plastic. In one form, the lever arm 208 flexes or bends more than the hub body 202 so the pieces can snap together more easily during manufacture and assembly. The suture or tension member 210 includes suture material that will be particularly useful in certain embodiments and/or a variety of other elongate materials and objects capable of being anchored can be used as an alternative to, or in addition to, suture material. These include various types of cords, filaments, chains, strings, wires and other similar objects having relatively slender profiles for extending through patient tissue.

Turning now to the sealing element 236, the sealing element 236 is sized and shaped to fit in a portion of the aperture 232 of the hub body 202. In this embodiment, the sealing element 236 has a body portion 281 that has a cylindrically tapered cross-sectional shape and spans between a base end 280 and a tip end 282. The sealing element 236 also includes a lumen 284 that spans between the base end 280 and the tip end 282 and the lumen 284 passes through the body portion 281. The base end 280 and the tip end 282 are each cylindrical in shape. In one embodiment, the length of the sealing element 236 is the same as the length of the aperture 232. As such, the base end 280 has a base diameter that corresponds to and is about the same size as a diameter of the aperture 232 that meets the exterior surface 234 of the hub body 202. In a second embodiment, the length of the sealing element 236 is longer than the length of the aperture 232. As such, the base end 280 has a base diameter that is larger than a diameter of the aperture 232 that meets the exterior surface 234 of the hub body 202 wherein the base end 280 and an adjacent portion of the sealing element 236 extend from the aperture 232. The body portion 281 tapers in diameter from the base end 280 to the tip end 282 such that the sealing element 236 substantially plugs or seals the aperture 232 from the base end 280 to the tip end 282 when the lever arm 208 is in a closed or locked position. The lumen 284 is sized to receive the tension member 210. In alternative embodiments, the sealing element 236 does not include a pre-formed lumen but instead the tension member 210 is attached to a needle which then passes through the sealing element 236 which has a solid cross-section to form a lumen in the sealing element 236.

The sealing element 236 is made from similar materials and techniques as sealing element 136. The lumen 284 in the sealing element 236 can be manufactured and assembled with the tension member 210 in a variety of techniques similar to the lumen 184 in the sealing element 136.

Turning now to the third embodiment of a drainage catheter hub assembly 300 illustrated in FIG. 10, the catheter hub assembly 300 is similar to the catheter hub assembly 200; therefore, for the sake of brevity similar details will not be discussed again. In this illustrative arrangement, the catheter hub assembly 300 includes a hub body 302 and a lever arm 308 that is configured to attach to the hub body 302 to clamp a suture or a tension member therebetween. The catheter hub assembly 300 is configured to engage with a catheter tube to form a catheter system.

The hub body 302 also includes a lower body portion 318 opposite an upper portion 320 and a right face 322 opposite a left face (not illustrated). Each of the right face 322 and the left face includes a post 326 sized and configured to receive and retain the lever arm 308. In one form, the post 326 has a circular shape and extends a distance away from the right face 322 and the left face. The post 326 is sized and configured to engage a side opening 309 in the lever arm 308 such that the lever arm 308 is able to rotate about the post 326 as desired by the user or medical practitioner. The post 326 is configured to restrict movement of the lever arm 308 between unlocked and locked positions. The post 326 is configured to restrict movement of the lever arm 308 between 0 degrees and about 30 degrees relative to a longitudinal axis L of the hub body 302. Other embodiments can include different sizes, shapes, and configurations for the interactive features between the lever arm 308 and the hub body 302. For example, the lever arm 308 can include a pivot post and the hub body 302 can include a receptacle sized to receive the pivot post to engage and retain the pivot post therein and the lever arm 308.

The upper portion 320 of the hub body 302 has a raised portion 327 that receives the tension member. Correspondingly, the lever arm 308 has a receptacle (not illustrated) sized to receive the raised portion 327 when the lever arm 308 is in the closed or locked position similar to catheter hub assembly 100.

Turning now to the fourth embodiment of a drainage catheter hub assembly 400 illustrated in FIG. 11, the catheter hub assembly 400 is similar to the catheter hub assembly 200; therefore, for the sake of brevity similar details will not be discussed again. In this illustrative arrangement, the catheter hub assembly 400 includes a hub body 402 and a lever arm 408 that is configured to attach to the hub body 402 to clamp a suture or a tension member therebetween. The catheter hub assembly 400 is configured to engage with a catheter tube to form a catheter system.

The hub body 402 also includes a lower body portion 418 opposite an upper portion 420 and a right face 422 opposite a left face (not illustrated). Each of the right face 422 and the left face includes a receptacle or cavity 426 sized to receive and retain a post 428 on the lever arm 408 such that the lever arm 408 is able to rotate about the receptacle 426 as desired by the user or medical practitioner. The receptacle 426 is configured to restrict movement of the lever arm 408 between an unlocked position and a locked position. The receptacle 426 is configured to restrict movement of the lever arm 408 between 0 degrees and about 30 degrees relative to a longitudinal axis L of the hub body 402. Other embodiments can include different sizes and shapes or arrangements for the interactive features between the lever arm 408 and the hub body 402. For example, the hub body 402 includes a pivot post and the lever arm 408 and includes a receptacle sized to receive the pivot post to engage and retain the pivot post therein and the lever arm 408.

In one form, the drainage catheter hub of the application may be used as follows. Drainage and insertion sites are selected and prepared using appropriate known techniques and a guidewire is inserted into the drainage site. This description describes the "over-the-guidewire" introduction technique. Some physicians also use a "direct puncture" technique in some circumstances. This disclosure is equally useful when performing the direct puncture technique where a trocar is used in place of the guidewire. The drainage catheter hub is identical for both catheter introduction methods.

A catheter in accordance with FIG. 1 (or otherwise in accordance with this disclosure) is provided with catheter hub assembly 100 in the unlocked position of FIG. 2. A cannula (not shown) is then inserted into tube 106 of the catheter to maintain the distal end of the tube 106 in a straight configuration so that the catheter may be passed over the previously emplaced guidewire into the drainage site while monitoring using non-invasive imaging such as fluoroscopy, CT (computed tomography) or ultrasound to ensure that the proximal end is properly positioned within the cavity. The proximal end of the catheter including the drainage catheter hub will be outside of the patient's body close to the skin surface at the entry point into the body. At this point, the cannula and guidewire are removed.

When the cannula is removed, a restraining portion of tube 106 curls into its preformed unstressed end of the tubular member configuration. The physician then pulls upon tension member 110 to remove any slack and optionally to further curl the end of the tubular member. Lever arm 108 is then moved or rotated to its locked position (FIG. 4), compressing sealing element 136 to maintain the plurality of lever arm serrated teeth 150 in engagement with the plurality of hub serrated teeth 146 on the hub body 102 thereby trapping the suture or tension member 110 between the two toothed surfaces. Additionally, in the locked position the engagement portion 178 on the interior surface 162 of the lever arm 108 presses against the sealing element 136 to seal the aperture 132 and the lumen 184 around the tension member 110. The suture or tension member 110 can be simply cut close to the hub body 102 after the device is locked. The luer lock end 115 is then attached to an appropriate drainage collection system and fluid is drained as appropriate. Once the drainage procedure is completed and the catheter is to be removed, the drainage catheter hub is disconnected from the catheter. Lever arm 108 is then rotated to an unlocked position to release the tension member 110. This rotational movement releases the lever arm 108 and the catheter may now be removed from the cavity. A like procedure can be used when the drainage catheter hub is to be used for feeding purposes.

Any or all of the components described herein can be provided in a sterile pack for providing necessary parts, or a variety of parts, to a surgeon. For example, one or more predetermined types or sizes of catheters pre-engaged with a variety of drainage catheter hubs may be provided in a single sterile package or kit. A surgeon can choose the sizes or types of components he or she wishes to use during surgery. Alternatively, sterile kits containing predetermined sizes or types of components may be provided. Packages or kits of the components described herein can include additional devices or tools which may be useful in the particular medical procedure being performed.

Flexible tubular members suitable for use herein are well known in the art, and tubular member (catheter) 106 may be formed from any such well-known composition, such as polyether-urethane. Tubular member 106 will typically have, e.g., an outer diameter of between about 5 and 24 French, and a length of between about 15 and 40 cm. If desired, the distal portion, e.g., about the distal 5 cm, of the tubular member may have a hydrophilic coating. The tension member or suture may be formed of any compositions routinely used for tension members or sutures in the medical arts, such as monofilament nylon.

While the disclosure has been illustrated and described in detail in the drawings and foregoing description, the same is to be considered as illustrative and not restrictive in character, it being understood that only selected embodiments have been shown and described and that all equivalents, changes, and modifications that come within the spirit of the subject matter as defined herein or by the following claims are desired to be protected.

The invention claimed is:

1. A drainage catheter hub for use with a tension member and a drainage catheter, the drainage catheter hub comprising:
   a hub body defining a fluid passageway in communication with an aperture, the hub body adapted for attachment to the drainage catheter, the fluid passageway and the drainage catheter aligned for fluid flow therethrough;
   a sealing element configured to receive the tension member, the sealing element sized for and positioned in the aperture;
   and a lever arm attached to the hub body such that the lever arm is moveable between an unlocked position wherein the tension member is movable through the sealing element and a locked position wherein the tension member is restrained from movement through the sealing element, wherein the lever arm is configured to press against the sealing element to compress the sealing element to block fluid flow through the sealing element and the aperture.

2. The drainage catheter hub according to claim 1, wherein an exterior surface of the hub body includes a plurality of hub serrated teeth, and an interior surface of the lever arm includes a plurality of lever arm serrated teeth that are arranged and configured to engage the plurality of hub serrated teeth to retain the tension member aligned along a longitudinal axis of the hub.

3. The drainage catheter hub according to claim 1, wherein an exterior surface of the hub body includes a centering tab configured to align the tension member along a longitudinal axis of the hub body and an interior surface of the lever arm includes a pocket sized to receive the centering tab in the locked position.

4. The drainage catheter hub according to claim 1, wherein the lever arm is rotatably connected to the hub body and an angle of rotation for the lever arm relative to a longitudinal axis of the hub body is restricted from 0 degrees in the locked position to about 30 degrees in the unlocked position.

5. The drainage catheter hub according to claim 1, wherein the lever arm includes a pair of protrusions to engage the hub body and retain the lever arm in a locked position.

6. A drainage catheter for introduction in a patient, comprising:
   an elongated tubular member, the tubular member having a distal end adapted for insertion into a patient, a proximal end, and a passageway extending longitudinally therethrough, the passageway sized to receive a tension member therein;
   a drainage catheter hub attached to the proximal end of the tubular member, the drainage catheter hub includes a lever arm connected to a hub body and a sealing element configured to receive the tension member;
   wherein the hub defines an aperture sized to receive the sealing element, the aperture extending from and communicating with the passageway of the tubular member to an exterior surface of the hub body, the aperture and the passageway aligned for fluid flow therethrough;
   and wherein the lever arm is configured to move between a locked position wherein the tension member is restrained from movement through the sealing element and an unlocked position wherein the tension member is movable through the sealing element, and the lever arm is further configured to compress the sealing element.

7. The drainage catheter according to claim 6, wherein the lever arm is rotatably connected to the hub body.

8. The drainage catheter according to claim 7, wherein an angle of rotation for the lever arm relative to a longitudinal axis of the hub body is restricted from 0 degrees in the locked position to about 30 degrees in the unlocked position.

9. The drainage catheter according to claim 6, wherein the hub body includes a post and the lever arm includes a hole sized to receive the post therein to connect the lever arm to the hub body.

10. The drainage catheter according to claim 6, wherein the exterior surface of the hub body includes a centering tab configured to align the tension member along a longitudinal axis of the hub body.

11. The drainage catheter according to claim 10, wherein the centering tab includes a vertical leg that extends from the exterior surface of the hub body to connect to a horizontal leg with a groove therebetween sized to retain the tension member.

12. The drainage catheter according to claim 10, wherein the exterior surface of the hub body includes a plurality of hub serrated teeth positioned between the aperture and the centering tab, and an interior surface of the lever arm includes a plurality of lever arm serrated teeth that are arranged and configured to engage the plurality of hub serrated teeth to retain the tension member aligned along the longitudinal axis of the hub.

13. The drainage catheter according to claim 6, wherein the aperture includes a base end having a first diameter and in communication with the passageway and a tip end having a second diameter that is larger than the first diameter, the tip end in communication with the exterior surface of the hub, and the aperture having a body portion that spans between the base end and the tip end wherein the body portion has a variable diameter sized to receive a portion of the sealing element therein and to block fluid flow through the base end of the aperture.

14. The drainage catheter according to claim 6, wherein the lever arm is configured to compress the sealing element to block fluid flow through the sealing element and the aperture when the lever arm is in the locked and unlocked positions.

15. A method for introducing a drainage catheter in a patient, comprising:
   introducing a distal end of an elongated tubular member of a catheter into a patient, the tubular member also having a proximal end and a passageway extending longitudinally through the tubular member, the catheter also including a catheter hub attached to the proximal end of the tubular member, the catheter hub including a hub body defining an aperture in fluid communication with the passageway and a sealing element received in the aperture, the catheter hub further including a lever arm connected to the hub body;

with the lever arm in an unlocked position, applying tension to a tension member extending through the sealing member and aperture and through the passageway, so as to provide a tensioned condition of the tension member with a portion of the distal end of the elongated tubular member in a curled shape; and moving the lever arm to a locked position to restrain the tension member from movement and cause an interior surface of the lever arm to press against the sealing element, wherein said moving the lever arm causes retention of the tension member between a plurality of teeth on the hub body and a plurality of teeth on the lever arm.

16. The method of claim 15, comprising:

during said introducing, passing the distal end of the elongated tubular member to a drainage site in a patient while having a cannula in the passageway, the cannula maintaining the distal end in a straight configuration, and removing the cannula whereupon a restraining portion of the elongated tubular member forms a curl.

17. The method of claim 15, wherein said moving the lever arm comprises rotating the lever arm relative to the hub body.

18. The method of claim 17, wherein the hub body includes a post and the lever arm includes a hole sized to receive the post therein to connect the lever arm to the hub body.

* * * * *